United States Patent

Roth

[11] 3,977,406
[45] Aug. 31, 1976

[54] MEDICAL SPONGES

[75] Inventor: Roy William Roth, New Canaan, Conn.

[73] Assignee: American Cyanamid Company, Stamford, Conn.

[22] Filed: June 19, 1974

[21] Appl. No.: 480,643

[52] U.S. Cl. ............................ 128/296; 128/156; 428/160
[51] Int. Cl.² ........................................ A61F 13/00
[58] Field of Search.... 128/132 R, 132 D, 155–156, 128/268, 284–285, 290 R, 293–296, 292; 161/132, 116, 124, 411; 264/321

[56] References Cited
UNITED STATES PATENTS

| | | | |
|---|---|---|---|
| 2,896,618 | 7/1959 | Schaefer | 128/296 |
| 3,156,242 | 11/1964 | Crowe, Jr. | 128/156 |
| 3,285,768 | 11/1966 | Habib | 161/123 |
| 3,378,432 | 4/1968 | Spencer | 161/123 |
| 3,464,415 | 9/1969 | Brownlee | 128/296 |
| 3,491,753 | 1/1970 | Milton et al. | 128/156 |
| 3,566,871 | 3/1971 | Richter | 128/296 |
| 3,587,583 | 6/1971 | Greenberg | 128/296 |

*Primary Examiner*—John D. Yasko
*Attorney, Agent, or Firm*—Frank M. Van Riet

[57] ABSTRACT

Hydrophilic sponges adapted for medical uses comprising texturized polyurethane foams embossed with various fused designs.

6 Claims, 2 Drawing Figures

MEDICAL SPONGES

BACKGROUND OF THE INVENTION

In the field of medical practice, there is known to be frequent need for sponging the body to remove therefrom body fluids such as blood, serum, plasma, lymph, spinal fluid, tissue fluid, urine, sweat, bile juice, digestive juice etc. That is to say, during a surgical incision it is necessary to sponge the areas approximate to the incision to remove blood and other fluids emanating therefrom. After entering the operative field, it is also customary to use sponges to isolate various organs from the field by packing them with the sponges to prevent them from interfering with the operation. Sponges of varying size and configuration are also utilized in such areas of surgery as ophthalmic surgery, neurosurgery, spinal surgery and the like for the same purpose.

Hydrophilic sponges prepared from polyurethane foams are well known in the art. For example, such a sponge is disclosed in U.S. Pat. No. 3,566,871. Similarly, compressed polyurethane foams have been disclosed as useful bandage components in U.S. Pat. No. 3,665,918. Additionally, U.S. Pat. Nos. 3,098,048; 3,149,000; 3,326,823 and 3,463,745 also specify various hydrophilic polyurethane foams and how they may be modified so as to render them useful for various applications, usually in the medical field.

While these foam products of the prior art are useful in many applications, they suffer from at least two main deficiencies which render them less attractive for other uses. The prime deficiency of these prior art materials resides in the tendency of the foam from which they are prepared to retain its elastic memory over the life of the material. As a result, the tendency of the material to "bounce back" into its original shape after having been folded, crumpled etc. destroys its usefulness where retention of shape is desired, if not necessary. This so called "drape" or "dead fold" of the foam is insufficient if some maximum degree of shape retention cannot be attained.

A second detrimental property of the known prior art polyurethane foams is their unsatisfactory "hand" i.e. the roughness or abrasive quality of their outer surface due to the exposed cells of the foam. In areas of use where a very limp hand is required in order not to aggravate the body part with which the material comes in contact, these prior art foams are unattractive and, in fact, useless.

SUMMARY

I have now found that the drape of polyurethane foams can be markedly improved, i.e. the resiliency of the foam can be effectively decreased, and the hand can be materially enhanced, by both embossing the foam with a specific pattern configuration and texturizing the foam, both under individual and specific conditions of temperature and pressure. As a result, the foam produced by my novel process can be folded or otherwise compressed or compacted, particularly for medical usage in a body cavity, without deleteriously reverting to its original shape. Additionally, my novel foam is more easily folded and it therefore can be made to fit into a smaller package resulting in substantial savings in marketing costs.

DESCRIPTION OF THE INSTANT INVENTION INCLUDING PREFERRED EMBODIMENTS

Figure 1:
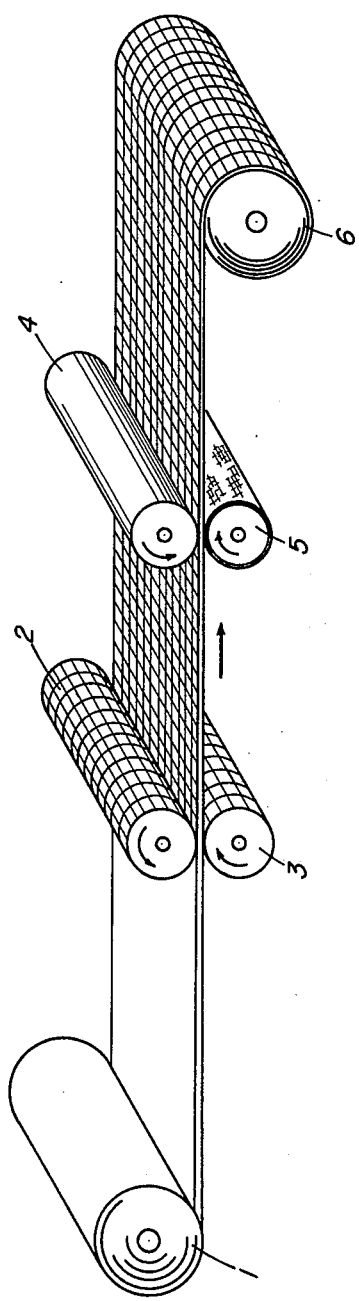
FIG. 1 is a isometric view of an embossing and texturizing means useful herein.

As mentioned above, the novel process of the present invention comprises a combined texturizing and embossing of hydrophilic polyurethane foam under a set of critical conditions.

Any known hydrophilic foam can be employed in my novel process with those set forth in the above U.S. references being exemplary. Specifically, both polyether and polyester based polyurethane foams may be employed. The foams may be hydrophilic as they are produced or they may be rendered hydrophilic by chemical modification thereof such as by adding a hydrophilic agent to the reaction mixture from which the foam is prepared. Polyurethane foams impregnated with a hydrophilic agent such as sodium lauryl sulfate, U.S. Pat. No. 3,665,918, may also be used, it being obvious that the reactants or impregnants used in the production of these foams cannot be of the type which would irritate or otherwise not be conductive to use within the human body. Surface coated foams can also be employed such as those disclosed in U.S. Pat. No. 3,566,871, it again being critical that the coating be medically acceptable.

Ether silicon surfactants such as those having the formula

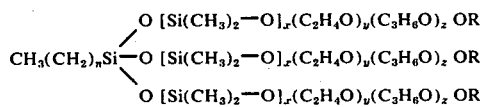

wherein $n$ is 2–4, inclusive, $x$ is 4–8, inclusive, $y$ is 15–19, inclusive, $z$ is 10–14, inclusive, and R is a lower alkyl ($C_1$–$C_4$) radical may be used to render non-hydrophilic foams hydrophilic. Those hydrophilic foams taught in French Patent Nos. 1,501,616 and 1,505,647, U.S. Pat. No. 3,249,465 and in Netherlands Application No. 6,513,233 may also be used, these and the above applications and patents disclosing useful foams hereby being incorporated herein by reference. Typical foams have a specific gravity of less than about 0.004 and a cell size of less than about 1.5 mm.

I have now found that two foam treatment steps combine to obtain a cooperative result in that the resultant foam has properties better than a foam produced by treating it with either of the steps individually.

According to the instant invention, these hydrophilic foams are texturized at a temperature of from about 50° to about 300°F., preferably from about 60° to about 90°F. and a pressure of from about 2,000 psi to about 3,000 psi, preferably from about 2,200 psi to about 2,600 psi. The texturizing is accomplished by passing the hydrophilic foam through two nip rollers, one preferably steel covered with cotton and the other polished steel. The texturizing flattens the foam and breaks all the reticulated cells at the surface thereof so as to create greater absorbancy and a better hand in the resultant foam. The foam is not permanently compressed by the texturizing step and bounces back to its original thickness after a few days.

The embossing procedure creates a fused design in the foam and causes a permanent deformation or compression thereof to the extent that its original thickness of from about 1/16 inch to about ½ inch, at the area where embossing occurs, is reduced from about 25 to about 95 percent. That is to say, the design which is embossed into the foam is done so to the extent that the foam thickness where the design is imparted is reduced 25–95 percent. The embossing is carried out on the hydrophilic foam, before or after the texturizing, at a temperature ranging from about 250° to about 350°F., preferably about 280° to about 340°F. and at a pressure of from about 1,000 psi to about 2,000 psi, preferably from about 1,250 psi to about 1,750 psi. The embossing is preferably accomplished by feeding the foam through two nip rollers as above, with regard to texturizing, however, one roller is preferably formed of a nylon base and the embossing roller is formed of embossed steel. Additionally, horizontal presses or male-male matched rollers may be used.

In order to create the highly satisfactory medical sponges having the desired properties mentioned above, it is necessary that the design embossed thereon during the embossing step have a particular configuration. That is to say, in order to create the desired degree of drape in the resultant foam sponge, I have found that it must be embossed in a pattern composed of a series of continuous lines (or fused zones) no more than about one inch apart, each line of the design terminating at an edge of the foam sheet and intersecting another line thereof at least about every inch in any direction. As can be readily appreciated, many design configurations fall within the class of patterns and I have found that any such design will function properly so as to materially enhance the drape of the resultant foam product.

While not wishing to be held to any particular theory with regard to why the pattern so functions, it is believed that the embossed lines or sections flowing in a multitude of directions completely and unbrokenly across the foam sheet cause areas where folding or crumpling may more easily occur and since these areas are compressed or fused tightly, the elastic memory of the polyurethane foam at these points is decreased. As a result, the sheet is more likely to retain its "new" folded identity rather than to return to its old.

Examples of suitable patterns which may be embossed into the polyurethane foam include squares, rectangles, diamonds, triangles, polygons, etc. as well as random, nongeometric shapes and designs which conform to the above definition.

The sponges of the instant invention can be further modified by affixing thereto radiopaque materials such as vinyl plastics, polyvinyl chloride etc. containing X-ray grade barium sulfate (U.S. Pat. No. 3,736,935), retrieval bands or devices such as strings, threads or loops of rayon, cotton, etc. (U.S. Pat. No. 3,566,871) and/or materials detectable by magnetodiode such as nylon or another similar material carrying magnetized barium ferrite therein (U.S. Pat. No. 3,587,583). These materials may be applied to the foam by such means as intertwining, sewing, adhering, spot heat welding, ultrasonic welding and the like. However, it is preferred that they be added during the texturizing and/or embossing steps by utilizing as the carrying means a piece or section of a suitable thermoplastic polymer which becomes slightly tacky or moldable at the temperatures of these steps and is compressed into the polyurethane foam due to the pressure imparted thereto by the rollers.

Figure 2:
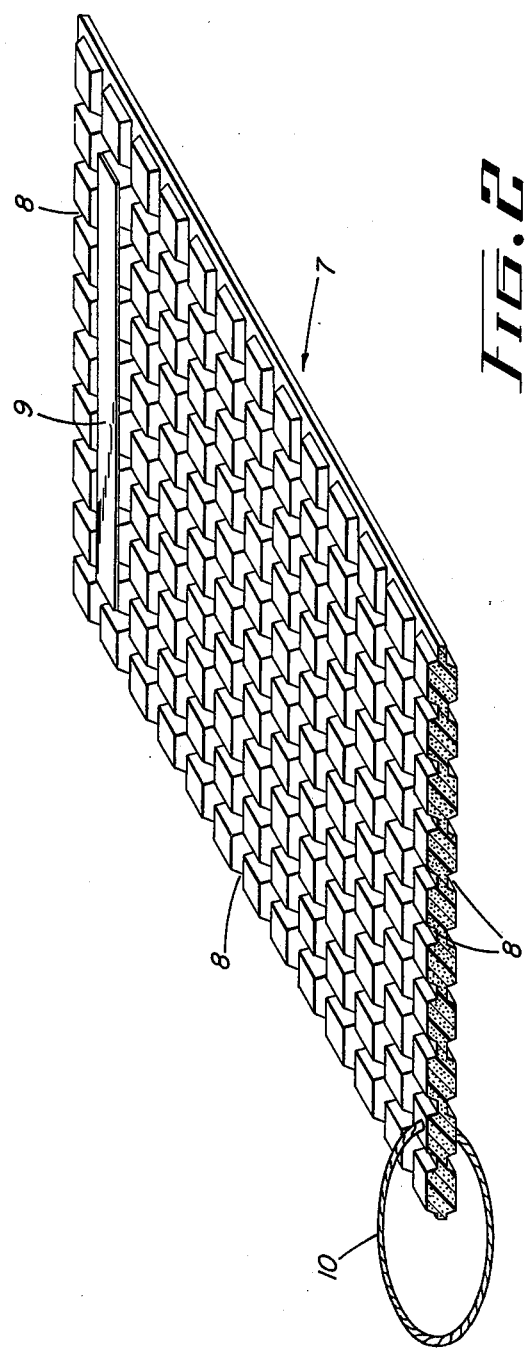
FIG. 2 is an isometric view of an enlarged section of the instant embossed and texturized foam.

Clarification of the instantly disclosed method and product may be had by reference to FIGS. 1 and 2 of the drawing. In FIG. 1, a roll of commercially available, hydrophilic polyurethane foam 1 is unwound and fed through two nip rollers 2 and 3 so as to emboss it with the design thereon. Roller 2 is the basic embossing roller and is formed of embossed steel while roller 3 is preferably formed of a nylon base. The embossed foam is then fed through rollers 4 and 5 whereby it is texturized as described above. Roller 4 is preferably of polished steel and roller 5 is preferably steel covered with cotton. The embossed and texturized foam is then wound into roll 6 for storage or packaging.

FIG. 2 represents a section of texturized and embossed foam 7 showing the pattern thereon comprising embossed lines 8 which flow across one another completely and unbrokenly across the sheet. The depicted pattern of squares are closely spaced and the lines 8 terminate at the edge of the foam. A radiopaque material 9 is shown affixed to one end thereof and a retrieval band 10 is shown threaded therethrough.

The following examples are set forth for purposes of illustration only and are not to be construed as limitations on the instant invention except as set forth in the appended claims. All parts are by weight unless otherwise specified.

EXAMPLE 1

Four 14½ × 10¼ inches samples of a commercially available hydrophilic polyurethane foam having a thickness of about ⅛ inch are designated as Samples 1–4. Sample 1 is utilized as a control. Sample 2 is embossed with a screenlike grid pattern, the continuous lines of which intersect each other at about every ¼ inch at a pressure of 1,500 psi and a temperature of 320°F. using an embossed steel roll and a nylon roll at a speed of 50 feet/minute. Sample 3 is texturized at a pressure of 2,400 psi and a temperature of 75°F. using a polished steel roll and a cotton covered steel roll at an identical speed. Sample 4 is both embossed as with Sample 2 and texturized as with Sample 3. Sample 1 has a tough spongy feel, is very stiff and bounces back almost immediately to substantially a flat sheet (one fold only) upon crumbling it into one's fist and placing it upon a flat surface. Sample 2 has the exact feel of Sample 1 but is more supple. When placed on a flat surface in a crumpled condition the sample almost immediately bounces back to a three-draped (folded) pile. Sample 3 has a smoother feel than either of Samples 1 or 2 but is very stiff and almost immediately bounces back when placed on a flat surface in a crumpled condition to a two-draped (folded) pile. Sample 4 has a softer feel and is more supple than any of the other Samples. The Sample bounces back to a three fold condition less rapidly than any of the three previous Samples.

When subjected to ASTM D-1388, option A, test procedure, the results are as follows:

| Sample 1 | | 4.65 cm. |
|---|---|---|
| Sample 2 | Bottom Surface | 3.00 cm. |
|  | Top Surface | 2.50 cm. |
| Sample 3 | | 2.90 cm. |

| Sample 4 | 1.90 cm. |
| --- | --- |

EXAMPLE 2

The procedure of Example 1 is again followed except that the hydrophilic polyurethane foam is prepared from 100 parts of a polyether polyol (prepared by reacting a 1:2 molar mixture of ethylene oxide and propylene oxide with glycerol. The resultant product has a hydroxyl group on each of three chain ends and an overall molecular weight of about 3,000), one part of an ether silicon surfactant having the formula

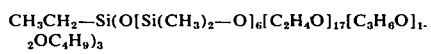

$CH_3CH_2-Si(O[Si(CH_3)_2-O]_6[C_2H_4O]_{17}[C_3H_6O]_{1.2}OC_4H_9)_3$ and 35.3 parts of a mixture of toluene diisocyanates with the isocyanate substitution in the 2,4 position in 80 percent and in the 2,6 position in 20 percent of the mixture, with 0.9 part of a solution of 33 percent triethylene diamine in dipropylene glycol and 0.15 part of stanneous octoate and 2.6 parts of water. The foam has a tensile strength of 13 psi and an elongation of 150 percent. When the foam is treated as in Example 1, Sample 4, an excellent product having better hand and drape than the other Samples and suitable as a laparotomy pad is recovered. It has the feel of a chamois and excellent drape.

EXAMPLE 3

The procedure of Example 1 is again followed except that the foam is produced as set forth in French Patent No. 1,501,616. The Samples show similar results when treated as set forth therein.

EXAMPLE 4

Four Samples are prepared from a foam produced as set forth in French Patent No. 1,505,647 and they are conditioned as set forth in Example 1 except that the embossed pattern is in the shape of diamonds, the continuous lines intersecting at every ½ inch. Again the Sample both embossed and texturized is the more desirable of the four with regard to feel and drape.

EXAMPLE 5

Four hydrophilic polyurethane Samples produced from foam manufactured as in Netherlands Application No. 6,513,233 are prepared as in Example 1 except that the order of treatment of Sample 4 is reversed. Again Sample 4 shows better properties according to the ASTM test set forth therein.

EXAMPLES 6–9

The procedure of Example 1 is again followed except that the embossed design is as described below. In each instance, the Sample which is both embossed and texturized has better properties of hand and drape than the other three which are not so treated.

EXAMPLE 6

Triangles embossed; ¾ inch intersection of continuous lines in all directions.

EXAMPLE 7

Double lines in each direction (length and width) of foam sheet, 1/32 inch apart, intersecting every inch in each direction.

EXAMPLE 8

A multitude of random continuous lines in varied directions, each ending at an edge of the sheet but intersecting at random distances of not more than 1 inch along each line.

EXAMPLE 9

Wavy, continuous lines diagonally across sheet spaced no more than 1 inch apart in the same direction and intersecting others at not more than 1 inch intervals.

EXAMPLE 10

A 1 × 2 inch section of the embossed and texturized Sample of Example 1 is modified by affixing to it a cotton thread 17 inches long by spot heat welding with polyethylene. The resultant device is used in neurosurgery without aggravation of membranes.

EXAMPLE 11

The procedure of Example 2 is again followed except that in the production of Sample 4 a thin strip of black polyvinyl chloride containing 63 percent of X-ray grade barium sulfate is placed atop the foam before it is embossed. The heat and pressure of the embossing process causes the strip to tenaciously adhere to the foam. The strip can be detected by X-ray detection means.

EXAMPLE 12

The procedure of Example 11 is again followed except that the polyvinyl chloride strip is replaced by a polyvinyl acetate strip containing 37 percent magnetized barium ferrite therein. The strip adheres tenaciously and can be detected by magneto-diode detection means.

EXAMPLES 13 AND 14

The procedure of Example 1 is again followed except that the foams used are produced as in (13) U.S. Pat. No. 3,665,918 and (14) U.S. Pat. No. 2,956,310. Again, excellent products are produced when the Sample 4 treatment is practiced thereon as compared to the other three Samples.

EXAMPLE 15

A large roll of commercially available hydrophilic polyurethane foam is continuously fed through texturizing and embossing equipment as described in Example 1. The resultant foam is then cut into 14 inch square sections and to each section is affixed a retrieval loop and a magnetic detection means. Each section is then folded, packaged and sterilized.

I claim:

1. A hydrophilic sponge, adapted for medical use, consisting essentially of a flexible, texturized, polyurethane foam sheet embossed with a fused design composed of a series of continuous, unbroken lines no more than about 1 inch apart, each end of each line terminating at an edge of the sheet and intersecting another line at least about every inch in each direction, the thickness of the area of said design being from about 25 to about 95 percent of the original thickness of said foam sheet, the remaining area being of the original thickness, substantially all of the reticulated cells at the surface of said sheet being broken.

2. A sponge according to claim 1 having a radiopaque material affixed thereto.

3. A sponge according to claim 1 having a retrieval means affixed thereto.

4. A sponge according to claim 1 having a magnetized material affixed thereto.

5. A sponge according to claim 1 which is sterile.

6. A medical sponge package comprising a sterile enclosure containing therein the sponge of claim 1 in sterile condition.

* * * * *